United States Patent [19]

Itoh et al.

[11] Patent Number: 4,892,754
[45] Date of Patent: Jan. 9, 1990

[54] PROCESS FOR PREPARATION OF WATER ABSORPTIVE COMPOSITE MATERIAL

[75] Inventors: Kiichi Itoh; Takeshi Shibano, both of Yokkaichi, Japan

[73] Assignees: Mitsubishi Petrochemical Company Limited, Tokyo; Uni-Charm Corporation, Kawanoe, both of Japan

[21] Appl. No.: 182,194

[22] Filed: Apr. 15, 1988

[30] Foreign Application Priority Data

Apr. 17, 1987 [JP] Japan ................................. 62-94465

[51] Int. Cl.$^4$ .................... B05D 3/06; B05D 3/02; B32B 27/00
[52] U.S. Cl. .................................. 427/54.1; 427/391; 427/392; 428/290; 526/930
[58] Field of Search ............... 427/372.2, 381, 382, 427/384, 385.5, 389.9, 391, 392, 54.1; 526/930, 317.1, 318.2; 428/290

[56] References Cited

U.S. PATENT DOCUMENTS

| | | | |
|---|---|---|---|
| 4,443,492 | 4/1984 | Roller | 428/290 |
| 4,703,067 | 10/1987 | Mikita et al. | 427/385.5 |
| 4,721,647 | 1/1988 | Nakanishi | 427/372.2 |
| 4,748,076 | 5/1988 | Saotome | 427/392 |
| 4,780,411 | 10/1988 | Piejko et al. | 427/384 |
| 4,828,911 | 5/1989 | Morman | 428/290 |
| 4,835,020 | 5/1989 | Itoh et al. | 427/384 |

Primary Examiner—Norman Morgenstern
Assistant Examiner—Marianne L. Padgett
Attorney, Agent, or Firm—Oblon, Spivak, McClelland, Maier & Neustadt

[57] ABSTRACT

There is provided a process for preparing a water absorptive composite material, which comprises the combination of the following steps:

(A) applying an aqueous solution of polymerizable monomers comprising as a main component acrylic acid, of which 20% or more of the carboxyl groups have been neutralized to its alkali metal salt or ammonium salt, to a prefabricated fibrous substrate;

(B) polymerizing the polymerizable monomers applied to said fibrous substrate to form a composite of a polymer derived from said polymerizable monomers and said fibrous substrate; and (C) irradiating ultraviolet rays onto said composite with its water content being 0.01 to 40 parts by weight per 1 part by weight of said polymer to obtain a water absorptive composite having a lower content of unpolymerized monomers than said composite.

12 Claims, No Drawings

PROCESS FOR PREPARATION OF WATER ABSORPTIVE COMPOSITE MATERIAL

BACKGROUND OF THE INVENTION

Field of the Art

This invention relates to a process for preparing a water absorptive composite material comprising a water absorptive polymer and a prefabricated fibrous substrate. More particularly, this invention relates to a process for preparing a water absorptive composite material in which a highly water absorptive polymer is held on a prefabricated substrate, comprising applying an aqueous solution of an acrylic acid type monomer to a prefabricated fibrous substrate, polymerizing the acrylic acid type monomer to obtain a precursor of the composite, which is further irradiated with ultraviolet rays.

The water absorptive composite material obtained by the process according to this invention can be advantageously used in the production of a variety of water absorptive materials, because it is excellent in water absorption properties, has an extremely low content of unpolymerized monomers and the highly water absorptive polymer is held with good stability on the fibrous substrate.

Prior Art

Materials such as paper, pulp, nonwoven fabric, spongy urethane resins and the like have hitherto been used as water retentive materials for a variety of sanitary goods such as a sanitary napkin, paper diaper and the like and a variety of agricultural materials. However, these materials have a water absorption capacity of no more than 10–50 times their own weight, which will cause problems that an extensively increased bulk of the material is required for absorbing or retaining a large amount of water and that water is easily released from the material in which water has been absorbed on pressing it.

There have recently been proposed a variety of highly water absorptive polymer materials in order to settle the aforementioned problems of the water absorptive materials of this kind. For instance, there have been proposed a graft polymer of starch (Japanese Patent Publication No. 46199/78, etc.), a denaturated cellulose (Unexamined Published Japanese Patent Application No. 80376/75, etc.), a crosslinked water soluble polymer (Japanese Patent Publication No. 23462/68, etc.), a self-crosslinking polymer of an alkali metal salt of acrylic acid (Japanese Patent Publication No. 30710/79, etc.), and the like.

However, these highly water absorptive polymer materials, while having a relatively high level of water absorption properties, are obtained as powder in most cases. Therefore, in order to use them for sanitary goods such as a sanitary napkin, paper diaper or the like, it is necessary to disperse them homogeneously on such substrates as tissue paper, nonwoven fabric, cotton or the like. However, the polymer powder having been dispersed in such a manner is difficult to be firmly held on the substrate and often agglomerate partially. Also, swollen gel after water absorption will easily move from the substrate without being held firmly on it. Therefore, if it is used for a paper diaper, for example, it will give the feeling of stiffness upon urination accompanied with the extremely uncomfortable feeling on wearing. Furthermore, in a process for obtaining an absorber by dispersing such a powdery polymer as described above on a substrate, the absorber will be very expensive because of complicated procedures for powder handling and of problems on processes for efficiently conducting uniform dispersion.

As a method for obviating these problems, there is disclosed a process for producing a water absorptive composite in which an aqueous solution of an acrylic acid type monomer is applied in a previously determined pattern to a prefabricated fibrous substrate to obtain a composite, which is then irradiated with electromagnetic radiation or corpuscular ionizing radiation to convert the acrylic acid type monomer into a highly water absorptive polymer (Unexamined Japanese PCT Patent Publication No. 500546/82). According to this process, uniform dispersion and stable holding of the aforementioned powder on a substrate are considerably improved. However, since electromagnetic radiation or corpuscular ionizing radiation is employed for converting the monomer into the high water absorptive polymer in this process, the highly water absorptive polymer inherent to the specific monomer tends to be crosslinked excessively. As the result, the composite obtained will exhibit extremely poor properties as an absorber. Especially its water absorption capacity will be of a level of only half or less of that of the composite obtained by using the aforementioned highly water absorptive powdery polymer.

Further, in Japanese Patent Publication No. 199866/82 is disclosed a process in which an aqueous monomer solution of an alkali metal salt of acrylic acid and a crosslinking agent is applied to a fibrous substrate, followed by irradiation with ultraviolet rays to convert the monomer into a water absorptive polymer. This process may be regarded, in view of its technical level, as being within the scope of the aforementioned prior art.

More recently, Unexamined Published Japanese Patent Application No. 149609/85 discloses a process for preparing a water absorptive composite material comprising previously impregnating a water absorptive organic material with an aqueous solution of an acrylic acid type monomer and adding thereto in a mist form a water soluble radical polymerization initiator, or, a water soluble radical polymerization initiator and a water soluble reducing agent to effect polymerization. In this process, however, the water soluble polymerization initiator is added after the water absorptive organic material has been impregnated with the acrylic acid type monomer. Thus, although the polymerization initiator is added in a mist form, it is very difficult to completely polymerize the monomer because of occurrence of "uneven polymerization" and as the result the amount of the residual monomers is at a high level, which will cause safety problems and lead to lowering of the properties of the resulting product, especially with respect to its water absorption capacity.

Possible Countermeasure

The, present inventors have already proposed in Japanese Patent Application No. 193403/85 a method that an aqueous solution of an acrylic acid type monomer having a monomer concentration of 25% by weight or more and either a water soluble radical polymerization initiator or a water soluble radical polymerization initiator and a water soluble reducing agent are previously mixed homogeneously and the mixture is applied in a mist form to a prefabricated fibrous substrate so that the resulting highly water absorptive polymer in the fibrous substrate will have a diameter in the range of 30–500 μm, followed by polymerization; in Japanese Patent Application No. 202908/85 a method that an aqueous solution of an acrylic acid type monomer containing a small amount of a crosslinking agent and either a water soluble radical polymerization initiator or a water soluble radical polymerization initiator and a water soluble reducing agent are previously mixed homogeneously and the mixture is applied in a mist form to a prefabricated fibrous substrate so that the resulting highly water absorptive polymer in the fibrous substrate will have a diameter in the range of 30–500 μm, followed by polymerization; in Japanese Patent Application No. 238421/85 a method that an aqueous solution of an acrylic acid type monomer containing a small amount of a crosslinking agent and an oxidizing radical polymerization initiator are previously mixed and the mixture is applied to a fibrous substrate, and then an amine or a reducing agent is added to carry out polymerization; and in Japanese Patent Application No. 238420/85 a method that an aqueous solution of an acrylic acid type monomer containing a small amount of a crosslinking agent and an amine or a reducing agent are mixed, followed by application to a fibrous substrate and then addition of an oxidizing radical polymerization initiator to conduct polymerization; and the like.

It has been found according to these methods that polymerization proceeds very easily, "uneven polymerization" is appreciably reduced and a composite having a high water absorption capacity can be obtained. However, the water absorptive composite thus obtained is not always satisfactory in its water absorption velocity and unpolymerized monomers still remain in it, thus causing problems on use for sanitary goods such as a sanitary napkin, paper diaper and the like.

SUMMARY OF THE INVENTION

Object of the Invention

This invention is an improvement of water absorptive composites described in Unexamined Japanese Patent Publication No. 500546/82 and Unexamined Published Japanese Patent Application No. 149609/85 and proposed by the present inventors in Japanese Patent Application Nos. 93403/85, 202908/85, 238421/85 and 238420/85, providing a process for preparing very easily under a moderate condition a water absorptive composite material which is excellent in water absorption properties, especially in water absorption velocity and has an extremely reduced amount of unpolymerized monomers.

The Invention

The present inventors have conducted an intensive research in order to solve the aforementioned problems. As a result, they have found that a water absorptive composite material which is excellent in water absorption properties, especially in water absorption velocity, and has an extremely reduced amount of unpolymerized monomers and in which the highly water absorptive polymer is held with good stability on the fibrous substrate, can be obtained very easily at low cost by applying an aqueous solution of an acrylic acid type monomer to a prefabricated substrate to polymerize the acrylic acid type monomer followed by irradiation with ultraviolet rays.

Thus, the process for preparing the water absorptive composite material according to this invention is characterized by the combination of the following steps:

(A) applying an aqueous solution of a polymerizable monomer comprising as a main component acrylic acid, of which 20% or more of the carboxyl groups have been neutralized to its alkali metal salt or ammonium salt, to a prefabricated fibrous substrate, (B) polymerizing the polymerizable monomers applied to said fibrous substrate to form a composite of a polymer derived from said polymerizable monomer and said fibrous substrate, and (C) irradiating ultraviolet rays onto said composite with its water content being 0.01 to 40 parts by weight per 1 part by weight of said polymer to obtain a water absorptive composite having a lower content of unpolymerized monomers than said composite.

The process for preparing the water absorptive composite material of this invention is very advantageous in that most of the acrylic acid monomer applied to the prefabricated substrate are polymerized to form a highly water absorptive polymer whereby the composite material obtained has an increased water absorption capacity, and that since said highly water absorptive polymer is subjected to irradiation with ultraviolet rays, the composite material obtained has a high water absorption velocity, an extremely reduced amount of unreacted monomers, and, the highly water absorptive polymer is held firmly on the fibrous substrate. Thus, a water absorptive composite material far better in properties as compared with those of the above mentioned prior art can be obtained easily and inexpensively.

Irradiation in step (C) of this invention is known as a polymerization and/or grafting means. The effect of this invention of reducing the amount of unreacted monomers or holding firmly the high water absorptive polymer on the fibrous substrate by conducting step (C) may be explained rather easily by the known function of such irradiation. However, it is believed totally unexpected, from the knowledge of the known function of the irradiation, that unpolymerized monomers are significantly reduced without any accompanying substantial influence on the polymer obtained in step (B), thus without entailing lowering of its water absorption capacity, by carrying out the irradiation under a specified condition of the water content of the polymer, i.e. 0.01 to 40 parts by weight per part by weight of the polymer.

DETAILED DESCRIPTION OF THE INVENTION

Steps (A) and (B)

Monomer

The monomer used in this invention contains as a main component acrylic acid, of which 20% or more, preferably 50% or more of the carboxyl groups are neutralized into its alkali metal salt or an ammonium salt. If the partial neutralization degree is less than 20%, the water absorption capacity of the resulting polymer will be significantly decreased.

In this invention, a polymer having a higher water absorption capacity may be obtained by adding in addition to the aforementioned acrylic acid and its salts one or two of the monomers copolymerizable therewith selected from the group consisting of 2-acrylamide-2methylpropanesulfonic acid, 2-acryloylethanesulfonic acid, 2-acryloylpropanesulfonic acid, methacrylic acid and alkali metal salts or ammonium salts thereof, (meth)acrylamide, N,N-dimethyl (meth)acrylamide, 2-hydroxyethyl (meth)acrylamide, 2-vinylpyridine, 2-hydroxyethyl (meth)acrylate, 2-hydroxypropyl (meth)acrylate, polyethylene glycol mono(meth)acrylate, N,N'-methylene bis(meth)acrylamide, polyethylene glycol di(meth)acrylate, trimethylolpropane tri(meth)acrylate, tetramethylolmethane tri(meth)acrylate, tetramethylolmethane tetra(meth)acrylate and dipentaerythritol hexaacrylate. The term "(meth)acryl" herein used means acryl and methacryl. It is also possible to incorporate other monomers copolymerizable with acrylic acid and acrylic acid salts including water soluble monomers such as itaconic acid, maleic acid, fumaric acid, vinylsulfonic acid and alkali metal salts or ammonium salts thereof and in addition less water soluble monomers such as alkyl esters of acrylic acid, for example methyl acrylate, ethyl acrylate and the like, providing that "an aqueous solution of a polymerizable monomer" of this invention is formed.

The "polymerizable monomer" of this invention comprises as a main component acrylic acid, of which 20% or more takes the salt form. Thus, the additional amount of the aforementioned copolymerizable monomer is usually less than 50 mol %, preferably 20 mol % or less.

For neutralization of the aforementioned acid monomers including acrylic acid, a hydroxide or bicarbonate of an alkali metal or ammonium hydroxide, preferably an alkali metal hydroxide, specifically sodium hydroxide, potassium hydroxide and lithium hydroxide may be used. Sodium hydroxide or potassium hydroxide is preferred from the standpoint of commercial availability, price, safety and the like.

In this invention, the polymerizable monomer comprising as a main component the aforementioned acrylic acid, of which 20% or more is present in its salt form, is applied in the form of an aqueous solution to a prefabricated fibrous substrate. Any concentration of the aqueous solution may be employed as far as it is suitable for the object. Specifically, it is preferably in the range of 30% by weight or more.

This aqueous solution may contain a variety of substances providing that they do not interfere with the object of this invention. As an example of such substances, there is mentioned a water soluble radical polymerization initiator (described in detail hereafter). The "aqueous solution" may be the one in which a small amount of a water soluble organic solvent is also present in solution, if desired.

Prefabricated fibrous substrate

A prefabricated substrate to which the aforementioned aqueous solution of the polymer is applied is specifically a substrate formed by loose fabrication of fiber such as a pad, a carded or air-laid web, tissue paper, a woven fabric like cotton gauze, knitted fabric or nonwoven fabric. The term "prefabricated" fibrous substrate herein used means the substrate which requires no web forming operation, though some operations such as cutting, bonding, shaping and the like may be required for incorporating the fibrous substrate into an article.

In general, absorptive fibers including cellulose fibers such as wood pulp, rayon, cotton and the like and/or polyester fibers are preferably used as a main component for the fibrous substrate. Other kinds of fibers such as those of polyethylene, polypropylene, polystyrene, polyamide, polyvinyl alcohol, polyvinyl chloride, polyvinylidene chloride, polyacrylonitrile, polyurea, polyurethane, polyfluoroethylene, polyvinylidene cyanide and the like may be also incorporated into the prefabricated fibrous substrate.

Application of an aqueous solution of the monomer and polymerization of the monomer (primary polymerization)

In this invention, the aforementioned monomer solution is applied to the aforementioned prefabricated fibrous substrate, and the monomer is polymerized on the fibrous substrate (primary polymerization).

In order to apply the aqueous monomer solution to the prefabricated fibrous substrate, there may be used any means or manner suitable for the object as long as the monomer is uniformly dispersed and held on the fibrous substrate and can be subjected to polymerization. One of the typical means therefor is to impregnate the aqueous monomer solution into the fibrous substrate or to spray the aqueous monomer solution onto the fibrous substrate.

The application of the monomer solution to the fibrous substrate is preferably conducted either in a manner that the solution applied will form a pattern of continued stripes along the fibers of the substrate or in a manner that the solution will make small spots uniformly dispersed on the substrate. As a specific method for practicing the former manner of application, there may be a method comprising impregnating the monomer solution into the prefabricated fibrous substrate or spraying a large quantity of the solution onto the substrate, and then removing by suction the monomer solution between the fibers, and a method comprising applying the monomer solution to the fibrous substrate by means of a roll coater. The latter manner of application is usually conducted by spraying the monomer solution onto the prefabricated fibrous substrate. It is desirable in this case of spraying to predetermine the condition so that the particle size of the solution upon spray will be 30 to 500 $\mu$m, preferably 30 to 200 $\mu$m in diameter.

For polymerizing the monomer which has been dispersed uniformly on the fibrous substrate as described above, any method can be used as far as it is suitable for the object. Typical methods include a method utilizing a water soluble radical polymerization initiator, more specifically, a method wherein a radical polymerization initiator has previously been added in the aqueous monomer solution and is decomposed on the fibrous substrate, a method wherein a radical polymerization initiator is applied uniformly in the form of a separate solution from the aqueous monomer solution to the fibrous substrate, to which the aqueous monomer solution has been applied, by spraying or the like and is decomposed on the fibrous substrate and a method wherein a radical polymerization initiator is applied uniformly in the form of a separate solution from the aqueous monomer solution to the fibrous substrate and then the aqueous monomer solution is uniformly applied thereto by spraying, coating or the like.

As another method for polymerization, there may be mentioned a method comprising initiating polymerization by irradiation with a high-energy radiation.

The water soluble radical polymerization initiator used in this invention is one well known in the art of polymer chemistry. There may be mentioned specifically inorganic or organic peroxides such as persulfates (ammonium salts, alkali metal salts, particularly potassium salts, or the like), hydrogen peroxide, di-tert-butyl peroxide, acetyl peroxide and the like. In addition to these peroxides, it is also possible to use such a radical polymerization initiator as an azo compound or the like, for example 2,2'-azobis(2-amidinopropane) dihydrochloride, providing that water solubility in a certain level can be obtained.

The polymerization is initiated by the decomposition of the radical polymerization initiator. Well known as a conventional means for decomposing the initiator is heating (As is often the case, when the initiator is contacted with the monomer the reaction mixture has already been raised to the decomposition temperature and thus the polymerization is initiated only by adding the polymerization initiator to the monomer without heating. This case is involved herein in the category of the decomposition by heating). Promotion of the decomposition of the polymerization initiator by means of a chemical substance is also well known in the art. When the polymerization initiator is a peroxide, a promoter of the decomposition thereof is a reducing compound (which is water soluble in this invention) such as an acidic sulfite, ascorbic acid and an amine for a persulfate, and a polymerization initiator comprising a combination of a peroxide and a reducing compound is well known in the art of polymer chemistry as "redox initiator". Thus, the term "polymerization initiator" herein used also involves initiator combined with such decomposition promoting substances, particularly redox initiators.

As a method for forming a redox system may be adopted any method as far as it is suited for the object. There may be mentioned, for example, a method of applying an aqueous monomer solution having previously dissolved therein an oxidative radical polymerization initiator to a fibrous substrate and then spraying thereon a reducing compound to form a redox system.

As regards the high-energy radiation, there may be used an electromagnetic radiation, corpuscular radiation and the like.

The polymerization by the above mentioned means, above all, by the action of a water soluble radical polymerization initiator of the monomer comprising as a main component acrylic acid, of which 20% or more is in the salt form, should give in principle a non-crosslinking water soluble polymer as far as a diethylenic monomer such as N,N'-methylene bis(meth)acrylamide is not present. However, it has in practice been known that crosslinking usually occurs between acrylic acids (or its salts) or the polymers thereof or/and between those and the fibrous substrate. Accordingly, the polyacrylic acid (salt) produced in this step may be considered as highly water absorptive polymer rather than water soluble polymer.

In addition, the polymerization by means of the water soluble radical polymerization initiator should be a substantially aqueous solution polymerization. Accordingly, step (B) should be conducted while avoiding an excessively dry state.

The amount of the monomer applied to the fibrous substrate during the step (A) is in a proportion of 1-10,000 parts by weight, preferably 10-1,000 parts by weight per 100 parts by weight of the fibrous substrate. The monomer thus applied should be polymerized in step (B) to an extent of 50% or more, preferably 80% or more. Rate of polymerization ordinarily reaches up to 85-99% in the step (B).

Some of the embodiments of the steps (A) and (B) are illustrated as follows:

(1) A method wherein an aqueous solution of an acrylic acid type monomer having a monomer concentration of 25% by weight or more and a water soluble radical polymerization initiator are previously mixed homogeneously and the mixture is applied in a mist form to a prefabricated fibrous substrate so that the resulting highly water absorptive polymer in the fibrous substrate will have a diameter in the range of 30–500 $\mu$m, followed by polymerization by heating if the polymerization initiator used is not a redox type (see Japanese Patent Application, No. 193403/85);

(2) A method wherein an aqueous solution of an acrylic acid type monomer containing a small amount of a crosslinking agent and a water soluble radical polymerization initiator are previously mixed homogeneously and the mixture is applied in a mist form to a prefabricated fibrous substrate so that the resulting highly water absorptive polymer in the fibrous substrate will have a diameter in the range of 30–500 $\mu$m, followed by polymerization by heating if the polymerization initiator used is not a redox type (see Japanese Patent Application No. 202908/85);

(3) A method wherein an aqueous solution of an acrylic acid type monomer containing a small amount of a crosslinking agent and an oxidizing radical polymerization initiator are previously mixed, the mixture is applied to a fibrous substrate and an amine or a reducing agent is added to form a redox system thereby initiating polymerization (see Japanese Patent Application No. 238421/85);

(4) A method wherein an aqueous solution of an acrylic acid type monomer containing a small amount of a crosslinking agent and an amine or a reducing agent are mixed, followed by application to a fibrous substrate and then addition of an oxidizing radical polymerization initiator to form a redox system thereby initiating polymerization (see Japanese Patent Application No. 238420/85); and (5) A method wherein an aqueous solution of an acrylic acid type monomer is previously impregnated into a fibrous substrate and then a water soluble radical polymerization initiator is added in a mist form, followed by polymerization by heating if the polymerization initiator used is not a redox type (see Japanese Patent Application No. 149609/85).

(6) A method wherein an aqueous solution of an acrylic acid type monomer is applied in a predetermined pattern to a fibrous substrate to form a composite, which is then irradiated with electromagnetic radiation or corpuscular radiation to initiate polymerization (Unexamined Japanese PCT Patent Publication No. 500 546).

Step (C)

Irradiation (secondary polymerization)

The composite comprising the highly water absorptive polymer obtained as above and the prefabricated fibrous substrate is then irradiated with ultraviolet rays.

The ultraviolet-rays irradiation may be conducted by the use of a conventional UV lamp. The conditions under which the irradiation is conducted such as irradiation intensity and time may differ depending on the type of the fibrous substrate used, the amount of the monomer applied to the substrate and the like. However, the irradiation is generally conducted using a UV lamp with an intensity of 10 to 200 W/cm, preferably 30 to 120 W/cm for 0.1 sec. to 30 min. with the distance between the UV lamp and the composite being 2 to 30 cm.

The water content in the composite during irradiation is generally 0.01 to 40 parts by weight, preferably 0.05 to 10 parts by weight per 1 part by weight of the polymer. Water content less than 0.01 part by weight or in excess of 40 parts by weight is not desirable, because the effect of decreasing unpolymerized monomers is significantly inferior. Limiting the water content to the above range may be effected either by controlling the water during the step (A) and/or step (B) or by adjusting it after the step (B).

The irradiation with ultraviolet rays on the composite according to this invention may be conducted under vacuum, in the presence of an inorganic gas such as nitrogen, argon, helium or the like, or in air.

The temperature on irradiation is not limited, and the object of irradiation can be satisfactorily achieved at room temperature.

The method to be employed for the irradiation is not limited either, and any method is employed in this invention as far as it is suited for the object. There may be mentioned, for example, the method of carrying out irradiation for a determined time on the composite in a static state and the method of continuous irradiation onto the composite moving on a belt conveyor.

EXAMPLES

Example 1

In a 100 cc conical flask, 13.1 g of sodium hydroxide (purity 95% by weight) was placed and dissolved in 39.0 g of pure water under ice cooling and the aqueous solution was neutralized by slowly adding 30 g of acrylic acid under ice cooling. The aqueous solution exhibited a neutralization degree of about 75% and a monomer concentration of about 45% by weight.

As a radical polymerization initiator, 0.05 g of potassium persulfate was added and dissolved in the aqueous solution, and deaeration was conducted using $N_2$.

Separately, 0.1569 g of a polyester nonwoven fabric was provided, and the whole surface of the nonwoven fabric was coated and impregnated with the above mentioned monomer solution. The weight of the monomer thus impregnated was 6.2 times the weight of the nonwoven fabric. The nonwoven fabric was placed in a constant temperature reaction bath which had preliminarily been deaerated with $N_2$ and heated to 90° C. Polymerization started immediately and a composite in which a highly water absorptive polymer comprising a partially neutralized self-crosslinked sodium polyacrylate was firmly held on the polyester nonwoven fabric was obtained.

Next, the composite was adjusted to a water content of about 20% by weight based on the polymer and then irradiation with ultraviolet rays was carried out onto the both sides of the composite respectively for two seconds using a UV lamp with an intensity of 80 W/cm with the distance between the UV lamp and the composite being 8 cm to obtain a water absorptive composite material.

The properties of the water absorptive composite material is shown below (as in the following Examples).

Example 2

In a 100 cc conical flask, 30 g of acrylic acid was placed and 9.3 g of pure water was added to and mixed with it. The mixture was neutralized by slowly adding 20.6 g of potassium hydroxide (85% by weight) under ice cooling and maintained at a temperature of 50° C. The aqueous solution exhibited a neutralization degree of about 75% and a monomer concentration of about 74% by weight.

Separately, as a radical polymerization initiator, 0.05 g of potassium persulfate was dissolved in 1 g of water and the aqueous solution was coated on the whole surface of 0.0985 g of a rayon nonwoven fabric.

Thereafter the monomer solution as the raw material was rapidly coated on the whole surfaces of the nonwoven fabric, the fabric was placed in a reaction bath which had been preliminarily deaerated with $N_2$ and maintained at a temperature of 90° C. The amount of the monomer thus impregnated was 10 times the weight of the nonwoven fabric. Polymerization started immediately and a composite in which a highly water absorptive polymer comprising a partially neutralized self-crosslinked potassium polyacrylate was firmly held on the rayon nonwoven fabric was obtained.

Next, the composite was adjusted to a water content of about 20% by weight based on the polymer and then irradiation with ultraviolet rays was carried out onto the both sides of the composite respectively for 5 seconds using a UV lamp with an intensity of 80 W/cm with the distance between the UV lamp and the composite being 10 cm to obtain a water absorptive composite material.

Example 3

In a 100 cc conical flask, 13.1 g of sodium hydroxide (purity: 95% by weight) was placed and dissolved in 39.0 g of pure water under ice cooling. The aqueous solution was neutralized by slowly adding 30 g of acrylic acid under ice cooling. The aqueous solution exhibited a neutralization degree of about 75% and a monomer concentration of about 45% by weight. 0.005 g of N,N'-methylene bisacrylamide as a crosslinking agent and 0.1 g of 2,2'-azobis(2-amidinopropane) dihydrochloride as a radical polymerization initiator were dissolved in the aqueous monomer solution, and deaeration was conducted with $N_2$.

Separately, 0.1505 g of a polyester nonwoven fabric was provided, and the whole surface of the nonwoven fabric was coated and impregnated with the above mentioned raw material. The amount of the monomer thus impregnated was 7.5 times the weight of the nonwoven fabric. The nonwoven fabric was placed in a constant temperature reaction bath which had preliminarily been deaerated with $N_2$ and heated to 90° C. Polymerization started immediately and a composite in which a highly water absorptive polymer comprising a partially neutralized sodium acrylate crosslinked with N,N'-methylene bisacrylamide was firmly held on the polyester nonwoven fabric was obtained.

Next, the composite was adjusted to a water content of about 40% by weight based on the polymer and then irradiation with ultraviolet rays was carried out onto the both sides of the composite respectively for three seconds using a UV lamp with an intensity of 80 W/cm with the distance between the UV lamp and the composite being 8 cm to obtain a water absorptive composite material.

Example 4

In a 100 cc conical flask, 30 g of acrylic acid was placed and 9.3 g of pure water was added to and mixed with it. The mixture was neutralized by slowly adding 20.6 g of potassium hydroxide (85% by weight) under ice cooling and maintained at a temperature of 70° C. The aqueous solution exhibited a neutralization degree of about 75% and a monomer concentration of about 74% by weight.

Separately, as a radical polymerization initiator, 0.2 g of potassium persulfate was dissolved in 3 g of water.

0.5869 g of a polyester nonwoven fabric was provided and maintained at a temperature of about 70° C. in a constant temperature bath. The aqueous radical polymerization initiator solution was mixed with the aqueous monomer solution mentioned above, and the mixture was immediately sprayed through a spraying nozzle onto the above mentioned nonwoven fabric. Polymerization started immediately and a composite in which a highly water absorptive polymer comprising a partially neutralized self-crosslinked potassium polyacrylate was firmly held on the polyester nonwoven fabric was obtained. The amount of the monomer thus coated was 12 times the weight of the nonwoven fabric, and the highly water absorptive polymer had a particle diameter in the range of 100–300 $\mu$m.

Next, the composite was adjusted to a water content of about 20% by weight based on the polymer and then irradiation with ultraviolet rays was carried out onto the both sides of the composite respectively for two seconds using a UV lamp with an intensity of 80 W/cm with the distance between the UV lamp and the composite being 8 cm to obtain a water absorptive composite material.

Example 5

In a 100 cc conical flask, 26.9 g of 25% aqueous ammonia was placed and neutralized by slowly adding 30 g of acrylic acid under ice cooling and heated to a temperature of 70° C. The aqueous solution exhibited a neutralization degree of about 95% and a monomer concentration of about 65% by weight.

Separately, 0.2 g of potassium persulfate as a radical polymerization initiator was dissolved in 3 g of water.

0.4695 g of a polyester nonwoven fabric was provided and maintained at a temperature of about 70° C. in a constant temperature bath. The aqueous radical polymerization initiator solution was mixed with the aqueous monomer solution mentioned above, and the mixture was immediately sprayed through a spraying nozzle onto the above mentioned nonwoven fabric. Polymerization started immediately and a composite in which a highly water absorptive polymer comprising a partially neutralized self-crosslinked potassium polyacrylate was firmly held on the rayon nonwoven fabric was obtained. The amount of the monomer thus coated was 8 times the weight of the nonwoven fabric, and the highly water absorptive polymer had a particle diameter in the range of 100–250 $\mu$m.

Next, the composite was adjusted to a water content of 50% by weight based on the polymer and then irradiation with ultraviolet rays was carried out onto the both sides of the composite respectively for two seconds using a UV lamp with an intensity of 80 W/cm with the distance between the UV lamp and the composite being 8 cm to obtain a water absorptive composite material.

Example 6

In a 100 cc conical flask, 13.1 g of sodium hydroxide (purity: 95% by weight) was placed and dissolved in 39.0 g of pure water under ice cooling. The aqueous solution was neutralized by slowly adding 30 g of acrylic acid under ice cooling. The aqueous solution exhibited a neutralization degree of about 75% and a monomer concentration of about 45% by weight.

0.1 g of N,N'-methylene bisacrylamide as a crosslinking agent was added and dissolved in the aqueous monomer solution, and the mixture was heated to 50° C. 0.2 g of potassium persulfate as a radical polymerization initiator was also dissolved in the above mentioned mixture.

Separately, 0.1598 g of a polyester nonwoven fabric was provided, and the whole surface of the nonwoven fabric was coated and impregnated with the above mentioned raw material, and the coated nonwoven fabric was maintained at a temperature of about 50° C. in a constant temperature bath. The amount of the monomer thus impregnated was 7.0 times the weight of the nonwoven fabric.

Next, an aqueous solution of 5% sodium hydrogen sulfite as a reducing agent was sprayed on the whole surface of the above mentioned nonwoven fabric. Polymerization started immediately and a composite in which a highly water absorptive polymer comprising a partially neutralized sodium acrylate crosslinked with N,N'-methylene bisacrylamide was firmly held on the polyester nonwoven fabric was obtained.

Next, the composite was adjusted to a water content of 30% by weight based on the polymer and then irradiation with ultraviolet rays was carried out onto the both sides of the composite respectively for two seconds using a UV lamp with an intensity of 80 W/cm with the distance between the UV lamp and the composite being 8 cm to obtain a water absorptive composite material.

Example 7

In a 100 cc conical flask, 30 g of acrylic acid was placed and 16.9 g of pure water was added to and mixed with it. The mixture was neutralized by slowly adding 20.6 g of potassium hydroxide (85% by weight) under ice cooling. The aqueous solution exhibited a neutralization degree of about 75% and a monomer concentration of about 65% by weight.

0.1 g of N,N'-methylene bisacrylamide as a crosslinking agent was added to and dissolved in the above mentioned monomer solution, and the mixture was heated to 40° C. 0.4 g of 31% aqueous hydrogen peroxide as a radical polymerization initiator was dissolved in the mixture.

0.1869 g of a polyester nonwoven fabric was provided, and the whole surface of the nonwoven fabric was coated and impregnated with the aforementioned raw material, and the nonwoven fabric thus treated was maintained at a temperature of 40° C. in a constant temperature bath. The amount of the monomer thus impregnated was 5.8 times the weight of the nonwoven fabric.

Next, an aqueous solution of 5% L-ascorbic acid was sprayed through a spraying nozzle onto the whole surface of the above mentioned nonwoven fabric. Polymerization started immediately and a composite in which a highly water absorptive polymer comprising a partially neutralized potassium polyacrylate crosslinked with N,N'-methylene bisacrylamide was firmly held on the polyester nonwoven fabric was obtained.

Next, the composite was adjusted to a water content of about 20% by weight based on the polymer and then irradiation with ultraviolet rays was carried out onto the both sides of the composite respectively for three seconds using a UV lamp with an intensity of 80 W/cm with the distance between the UV lamp and the composite being 8 cm to obtain a water absorptive composite material.

Example 8

In a 100 cc conical flask, 30 g of acrylic acid was placed and 16.9 g of pure water was added to and mixed with it. The mixture was neutralized by slowly adding 20.6 g of potassium hydroxide (85% by weight) under ice cooling. The aqueous solution exhibited a neutralization degree of about 75% and a monomer concentration of about 65% by weight.

0.1 g of N,N'-methylene bisacrylamide as a crosslinking agent was added to and dissolved in the above mentioned monomer solution, and the mixture was heated to 30° C. 0.2 g of L-ascorbic acid as a radical polymerization initiator was dissolved in the mixture.

0.2582 g of a polyester nonwoven fabric was provided, and the whole surface of the nonwoven fabric was coated and impregnated with the aforementioned raw material, and the nonwoven fabric thus treated was maintained at a temperature of 30° C. in a constant temperature bath. The amount of the monomer thus impregnated was 6.2 times the weight of the nonwoven fabric.

Next, 10% aqueous hydrogen peroxide was sprayed through a spraying nozzle onto the whole surface of the above mentioned nonwoven fabric. Polymerization started immediately and a composite in which a highly water absorptive polymer comprising a partially neutralized potassium polyacrylate crosslinked with N,N'-methylene bisacrylamide was firmly held on the polyester nonwoven fabric was obtained.

Next, the composite was adjusted to a water content of 25% by weight based on the polymer and then irradiation with ultraviolet rays was carried out onto the both sides of the composite respectively for two seconds using a UV lamp with an intensity of 80 W/cm with the distance between the UV lamp and the composite being 8 cm to obtain a water absorptive composite material.

Example 9

A water absorptive composite material was obtained in the same manner as in Example 1 except that the mixture of 28 g of acrylic acid and 2 g of methacrylic acid was used in place of the acrylic acid in Example 1.

Example 10

A water absorptive composite material was obtained in the same manner as in Example 3 except that the mixture of 30 g of acrylic acid and 3.5 g of 2hydroxyethyl methacrylate was used in place of the acrylic acid in Example 3.

Example 11

A water absorptive composite material was obtained in the same manner as in Example 7 except that the mixture of 30 g of acrylic acid and 3.5 g of acrylamide was used in place of the acrylic acid in Example 7.

Example 12

A water absorptive composite material was obtained in the same manner as in Example 7 except that the mixture of 30 g of acrylic acid and 5 g of 2-acrylamide-2-methylpropanesulfonic acid was used in place of the acrylic acid in Example 7.

Example 13

A water absorptive composite material was obtained in the same manner as in Example 7 except that the mixture of 30 g of acrylic acid and 0.5 g of 2-vinylpyridine was used in place of the acrylic acid in Example 7.

Example 14

A water absorptive composite material was obtained in the same manner as in Example 7 except that 0.182 g of polyethylene glycol (MW=600) diacrylate was used in place of N,N'-methylene bisacrylamide.

Example 15

A water absorptive composite material was obtained in the same manner as in Example 7 except that 0.171 g of tetramethylolmethane tetraacrylate was used in place of N,N'-methylene bisacrylamide.

Example 16

An aqueous solution of partially neutralized potassium acrylate (neutralization degree: 75%, monomer concentration: 65% by weight) containing 0.15% by weight of N,N'-methylene bisacrylamide as a crosslinking agent and 0.2% by weight of hydrogen peroxide as a radical polymerization initiator, the temperature of which was being maintained at about 40° C., was applied on and impregnated into a polyester nonwoven fabric of a width of 20 cm continuously by means of a roll coater at a rate of 30 m/min. The amount of the monomer impregnated was 6.5 times the weight of the nonwoven fabric.

Next, 5% aqueous solution of sodium thiosulfate was sprayed continuously onto the both sides of the nonwoven fabric. Polymerization started immediately and a composite in which a highly water absorptive polymer comprising a crosslinked product of a partially neutralized potassium polyacrylate was firmly held on the polyester nonwoven fabric was obtained.

The composite thus obtained, whose water content was found to be 25% by weight based on the polymer, was continuously passed through at a rate of 3 m/min. between two UV lamps with an intensity of 80 W/cm which were disposed opposite to each other respectively at a distance of 8 cm from the composite, and the nonwoven fabric thus irradiated with ultraviolet rays was subsequently wound up onto a reel to obtain a water absorptive composite material.

Example 17

In a 100 cc conical flask, 30 g of acrylic acid was placed and 16.9 g of pure water was added to and mixed with it. The mixture was neutralized by slowly adding 20.6 g of potassium hydroxide (85% by weight) under ice cooling. The aqueous solution exhibited a neutralization degree of about 75% and a monomer concentration of about 65% by weight.

0.3852 g of a polyester nonwoven fabric was provided, and the whole surface of the nonwoven fabric was coated and impregnated with the above mentioned raw material. The amount of the monomer impregnated was 7.5 times the weight of the nonwoven fabric.

Next, the nonwoven fabric having been impregnated with the aqueous solution of the partially neutralized potassium acrylate monomer was irradiated with electron beam at a dose of 20 Mrad by means of an electron beam generating apparatus equipped with an accelerator (DYNAMITRON). Polymerization started immediately and a composite in which a highly water absorptive polymer comprising a partially neutralized self-crosslinked potassium polyacrylate was firmly held on the polyester nonwoven fabric was obtained.

Next, the composite was adjusted to a water content of 30% by weight based on the polymer and then irradiation with ultraviolet rays was carried out onto the both sides of the composite respectively for two seconds using a UV lamp with an intensity of 80 W/cm with the distance between the UV lamp and the composite being 8 cm to obtain a water absorptive composite material.

Comparative Examples 1–17

The precursors obtained in Examples 1–17, that is the composites before the ultraviolet-rays irradiation are herein regarded as the composites in Comparative Examples 1–17, respectively.

For the water absorptive composite materials obtained in Examples and the composites obtained in Comparative Examples, the following tests were carried out to evaluate physiological saline absorption capacity and unpolymerized monomer concentration. The results are shown in Table 1.

A. Physiological saline absorption capacity

About 0.5 g of the composite or water absorptive composite material and about 200 g of a saline solution having a concentration of 0.9% by weight were precisely weighed, respectively and charged in a 300 ml beaker. The beaker was left standing for about 4 hours to swell the polymer satisfactorily with the solution. The beaker content was filtered through a 100-mesh sieve, and the amount of the filtrate is weighed and the physiological saline absorption capacity is calculated according to the following equation:

$$\text{Physiological saline absorption capacity} = \frac{\text{Charged amount of physiological saline (g)} - \text{Amount of filtrate (g)}}{\text{Charged amount of the composite or water absorptive composite material (g)}}$$

B. Unpolymerized monomer concentration 0.5 g of the composite or water absorptive composite material was precisely weighed and added to 1 liter of ion exchanged water in a 2 liter beaker to swell sufficiently with stirring for about 10 hours. The swollen polymer gel was filtered through a 200-mesh sieve and the filtrate was analyzed by a high pressure liquid chromatography.

Separately, standard monomer solutions having determined concentrations were prepared to make a calibration curve, and the absolute monomer concentration of the filtrate was determined with consideration for the degree of dilution (1/2000).

TABLE 1

| Example No. | Physiological saline absorption capacity (g/g) | Unpolymerized monomer concentration (ppm by wt.) |
|---|---|---|
| Example 1 | 45.3 | 358 |
| Example 2 | 46.6 | 498 |
| Example 3 | 37.2 | 256 |
| Example 4 | 71.3 | 351 |
| Example 5 | 69.8 | 304 |
| Example 6 | 43.2 | 422 |
| Example 7 | 58.2 | 405 |
| Example 8 | 51.2 | 351 |

TABLE 1-continued

| Example No. | Physiological saline absorption capacity (g/g) | Unpolymerized monomer concentration (ppm by wt.) |
|---|---|---|
| Example 9 | 43.5 | 287 |
| Example 10 | 48.3 | 311 |
| Example 11 | 72.1 | 455 |
| Example 12 | 61.5 | 387 |
| Example 13 | 70.1 | 299 |
| Example 14 | 62.9 | 332 |
| Example 15 | 63.2 | 391 |
| Example 16 | 61.5 | 421 |
| Example 17 | 17.3 | 58 |
| (bis) | | |
| Comp. Example 1 | 39.5 | 3586 |
| Comp. Example 2 | 42.1 | 25865 |
| Comp. Example 3 | 35.2 | 5255 |
| Comp. Example 4 | 67.8 | 5682 |
| Comp. Example 5 | 67.6 | 6821 |
| Comp. Example 6 | 41.3 | 15681 |
| Comp. Example 7 | 51.2 | 13482 |
| Comp. Example 8 | 48.8 | 15255 |
| Comp. Example 9 | 43.0 | 4157 |
| Comp. Example 10 | 45.2 | 5239 |
| Comp. Example 11 | 68.3 | 14376 |
| Comp. Example 12 | 55.2 | 11387 |
| Comp. Example 13 | 65.9 | 9845 |
| Comp. Example 14 | 59.3 | 8910 |
| Comp. Example 15 | 58.1 | 9123 |
| Comp. Example 16 | 55.3 | 12185 |
| Comp. Example 17 | 15.2 | 895 |

The water absorptive composite material obtained by the process of this invention, as apparent from the results shown in Table 1, has high water absorption capacity and an extremely low content of unpolymerized monomers and thus possessing very high safety, as compared with those in prior art. Further, the composite material handles easily because of its sheet form as compared with conventional powdery water absorptive resins, so that they can be used advantageously for the production of a variety of sanitary goods such as a sanitary napkin, paper diaper and the like.

The water absorptive composite material according to this invention, taking advantage of its excellent water absorption capacity and easy handling, can be also used for the production of a variety of materials for gardening and agriculture such as a soil conditioner and a water retaining agent which have recently attracted public attention.

What is claimed is:

1. A process for preparing a water absorptive composite material, which comprises the combination of the following steps of:
   (A) applying an aqueous solution of polymerizable monomers comprising as a main component acrylic acid, of which 20% or more of the carboxyl groups have been neutralized to its alkali metal salt or ammonium salt, to a prefabricated fibrous substrate;
   (B) polymerizing the polymerizable monomers applied to said fibrous substrate to form a composite of a polymer derived from said polymerizable monomer and said fibrous substrate; and
   (C) irradiating ultraviolet rays onto said composite with its water content being 0.01 to 40 parts by weight per 1 part by weight of said polymer to obtain a water absorptive composite having a lower content of unpolymerized monomers than said composite.

2. The process according to claim 1, wherein the polymerizable monomers comprises acrylic acid of which 20% or more of the carboxyl groups have been neutralized to its alkali metal salt or ammonium salt.

3. The process according to claim 1, wherein the polymerizable monomers contain up to 20 mol% of at least one of the monomers selected from the group consisting of 2-acrylamide-2-methylpropanesulfonic acid, 2-acryloylethanesulfonic acid, 2-acryloylpropanesulfonic acid, methacrylic acid and alkali metal salts or ammonium salts thereof, acrylamide, methacrylamide, N,N-dimethylacrylamide, N,N-dimethylmethacrylamide, 2-hydroxyethyl acrylamide, 2-hydroxyethyl methacrylamide, 2-vinylpyridine, 2-hydroxyethyl acrylate, 2-hydroxyethyl methacrylate, 2-hydroxypropyl acrylate, 2-hydroxypropyl methacrylate, polyethylene glycol monoacrylate, polyethylene glycol monomethacrylate, N,N'-methylene bisacrylamide, N,N'-methylene bismethacrylamide, polyethylene glycol diacrylate and polyethylene glycol dimethacrylate.

4. The process according to claim 1, wherein the fibrous substrate formed in step (A) comprises as a main component a cellulose fiber or/and a polyester type fiber.

5. The process according to claim 1, wherein the fibrous substrate formed in step (A) is a pad of loose fabric, a carded web, an air-laid web, a paper, a nonwoven fabric, a woven fabric or a knitted fabric.

6. The process according to claim 1, wherein the stage of applying the aqueous solution of the polymerizable monomers in the step (A) to the prefabricated fibrous substrate comprises spraying of said aqueous solution on to said fibrous substrate or impregnation of said fibrous substrate with said aqueous solution.

7. The process according to claim 1, wherein the amount of the polymerizable monomers applied to the fibrous substrate in step (A) is in a proportion of 1–10,000 parts by weight per 100 parts by weight of the fibrous substrate.

8. The process according to claim 1, wherein the polymerization in step (B) is carried out by means of a radical polymerization initiator.

9. The process according to claim 8, wherein the radical polymerization initiator comprises a redox type.

10. The process according to claim 1, wherein the irradiation with ultraviolet rays is carried out using a UV lamp with an intensity of 10 to 200 W/cm.

11. The process according to claim 10, wherein the irradiation is conducted for 0.1 sec. to 30 min. with the distance between the UV lamp and the composite being 2 to 30 cm.

12. The process according to claim 1, wherein the water content of the composite during the irradiation with ultraviolet rays is maintained at 0.05 to 10 parts by weight per 1 part by weight of said polymer.

* * * * *